US012695128B2

(12) United States Patent
Zhang et al.

(10) Patent No.: US 12,695,128 B2
(45) Date of Patent: Jul. 28, 2026

(54) METHOD FOR REGENERATED RAW MATERIALS FROM WASTE CADMIUM NICKEL BATTERY BASED ON SOLVENT EXTRACTION

(71) Applicants: South China University of Technology, Guangzhou (CN); Sichuan Changhong Battery Co., Ltd, Mianyang (CN)

(72) Inventors: Yongqing Zhang, Guangzhou (CN); Lei Zhou, Guangzhou (CN); Mingzhang Liu, Mianyang (CN); Juncong Fu, Guangzhou (CN); Jiang Chen, Mianyang (CN); Jihong Yi, Guangzhou (CN)

(73) Assignees: South China University of Technology, Guangzhou (CN); Sichuan Changhong Battery Co., Ltd, Mianyang (CN)

( * ) Notice: Subject to any disclaimer, the term of this patent is extended or adjusted under 35 U.S.C. 154(b) by 751 days.

(21) Appl. No.: 18/022,543

(22) PCT Filed: Jun. 10, 2022

(86) PCT No.: PCT/CN2022/098070
§ 371 (c)(1),
(2) Date: Feb. 22, 2023

(87) PCT Pub. No.: WO2023/206732
PCT Pub. Date: Nov. 2, 2023

(65) Prior Publication Data
US 2024/0274906 A1 Aug. 15, 2024

(30) Foreign Application Priority Data
Apr. 27, 2022 (CN) .......................... 202210452648.7

(51) Int. Cl.
*H01M 10/54* (2006.01)
*C01G 11/00* (2006.01)
(Continued)

(52) U.S. Cl.
CPC .......... *H01M 10/54* (2013.01); *C01G 11/003* (2013.01); *C01G 51/01* (2025.01); *C01G 53/01* (2025.01); *C07C 51/412* (2013.01)

(58) Field of Classification Search
CPC ....... H01M 10/54; C01G 51/01; C01G 53/01; C01G 11/003; C01G 11/00; C01G 51/00;
(Continued)

(56) References Cited

FOREIGN PATENT DOCUMENTS

| CN | 1617380 A | 5/2005 |
| CN | 1752232 A | 3/2006 |
| | (Continued) | |

OTHER PUBLICATIONS

English machine translation of CN108220608A (Year: 2018).*
(Continued)

*Primary Examiner* — Anthony J Zimmer
*Assistant Examiner* — Abdul-Rahman Yusuf Waleed Smari
(74) *Attorney, Agent, or Firm* — Bayramoglu Law Offices LLC

(57) ABSTRACT

A method for regenerating raw materials of waste Nickel-Cadmium batteries based on solvent extraction is disclosed. The method is used for disassembling, rinsing and shredding industrial waste from Nickel-Cadmium batteries. The solvent extraction technology is easy for large-scale and continuous production, and valuable metals such as cadmium, cobalt and nickel are extracted from the waste Nickel-Cadmium batteries to prepare products such as cadmium nitrate, cobalt nitrate, nickel nitrate which are directly used for producing raw materials for Nickel-Cadmium batteries.

(Continued)

No new waste salt and waste residues are generated in the process. High-efficiency separation and purification of all valuable metals during the regeneration of waste Nickel-Cadmium batteries and the full-life cycle regeneration cycle of Nickel-Cadmium batteries are achieved.

18 Claims, 1 Drawing Sheet

(51) Int. Cl.

| | |
|---|---|
| *C01G 51/01* | (2025.01) |
| *C01G 53/01* | (2025.01) |
| *C07C 51/41* | (2006.01) |

(58) Field of Classification Search
CPC ....... C01G 53/00; C07C 51/412; C07C 51/42; C07C 51/48; C07C 55/07; C22B 3/08; C22B 3/3842; C22B 3/3846; C22B 3/44; C22B 7/005; C22B 7/007; C22B 17/04; C22B 23/043; C22B 23/0484; Y02P 10/20
USPC .......................................................... 423/101

See application file for complete search history.

(56) References Cited

FOREIGN PATENT DOCUMENTS

| | | | |
|---|---|---|---|
| CN | 1287481 | C * | 11/2006 |
| CN | 100389520 | C | 5/2008 |
| CN | 101220412 | A | 7/2008 |
| CN | 101381816 | A | 3/2009 |
| CN | 101886177 | A | 11/2010 |
| CN | 101451246 | B | 1/2011 |
| CN | 102324592 | A | 1/2012 |
| CN | 108220608 | A | 6/2018 |
| CN | 108622943 | A | 10/2018 |
| EP | 0075978 | A2 | 4/1983 |
| KR | 101952608 | B1 | 2/2019 |

OTHER PUBLICATIONS

Reddy et al., "Chloride leaching and solvent extraction of cadmium, cobalt and nickel from spent nickel-cadmium, batteries using Cyanex 923 and 272" Journal of Power Sources 161, Jul. 2006, 1428-1434 (Year: 2006).*
Fernandes et al., "Hydrometallurgical route to recover nickel, cobalt and cadmium from spent Ni—Cd batteries" Journal of Power Sources 220, Aug. 2012, 286-291 (Year: 2012).*
Randhawa et al., "Leaching kinetics of spent nickel-cadmium battery in sulphuric acid" Hydrometallurgy 165, Sep. 2015, 191-198 (Year: 2015).*
GB/T 6009-2014, Anhydrous sodium sulfate for industrial use, China National Standards, 2014, pp. 1-10.

* cited by examiner

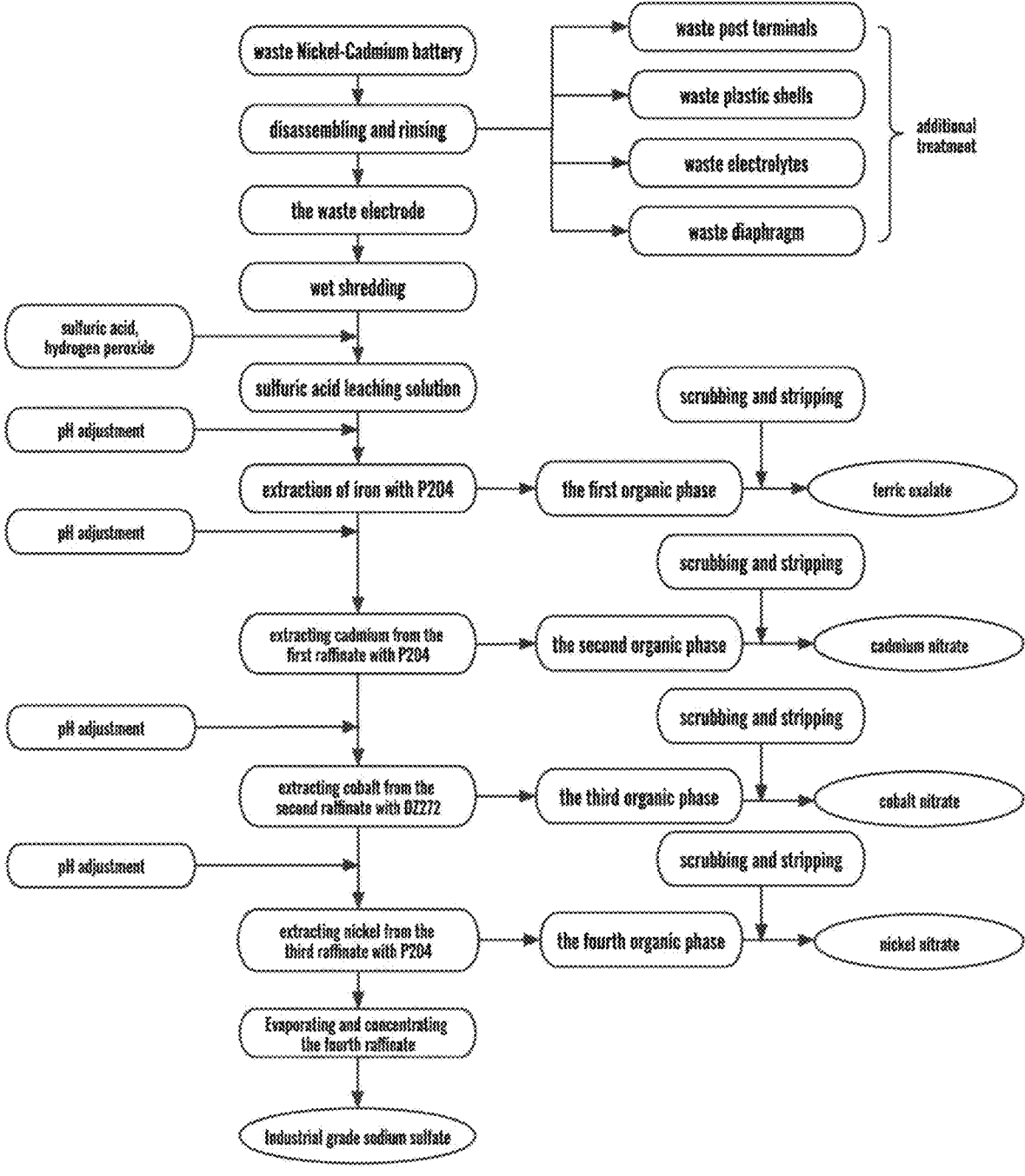

METHOD FOR REGENERATED RAW MATERIALS FROM WASTE CADMIUM NICKEL BATTERY BASED ON SOLVENT EXTRACTION

CROSS REFERENCE TO THE RELATED APPLICATIONS

This application is the national stage entry of International Application No. PCT/CN2022/098070, filed on Jun. 10, 2022, which is based on and claims priority to Chinese Application No. 202210452648.7, filed Apr. 27, 2022, the entire contents of which are incorporated herein by reference.

TECHNICAL FIELD

The invention relates to battery waste treatment, in particular to a method for regenerating raw materials of waste Nickel-Cadmium batteries based on solvent extraction, in particular to a method for regenerating raw materials of waste Nickel-Cadmium batteries based on sulfuric acid leaching-solvent extraction, and belongs to the field of resource recovery and recycling.

BACKGROUND

At present, most countries have legislation prohibiting the civilian use of Nickel-Cadmium batteries, but Nickel-Cadmium batteries are widely used in many fields due to their excellent low-temperature start-up performance, high-power current discharge characteristics, high reliability and long life and other irreplaceable advantages of other types of batteries. In the fields of aircraft, ships, transportation, military, large-scale grid energy storage, etc., their holdings are still maintained at a relatively high level.

The waste Nickel-Cadmium batteries are hazardous chemicals, which contain a large amount of valuable metals and have huge potential recycling value. Many countries such as Sweden, Switzerland, France, Germany, and the United States, have built specialized treatment devices for waste Nickel-Cadmium batteries, and at present, the application of specialized treatment of waste Nickel-Cadmium battery devices in China is still blank. Therefore, it is necessary to develop a stable and reliable recycling process for waste Nickel-Cadmium batteries that can meet the requirements of specialized large-scale production.

At present, the commonly used recycling methods for waste Nickel-Cadmium batteries at home and abroad are the pyrometallurgy, the hydrometallurgy and the pyrometallurgy-hydrometallurgy combination process. Among them, the pyrometallurgy is to separate and recycle various metals by using the difference in melting, boiling point and vapor pressure of various metals or metal oxides. For example, the European patent EP0075978A2 used pyrolysis to remove organic substances from waste Nickel-Cadmium storage batteries, and then the cadmium was evaporated and condensed by high-temperature distillation to form cadmium rods. The Chinese patent application CN102324592A adopted vacuum metallurgy to separate cadmium from waste Nickel-Cadmium batteries, and then used magnetic force to sort and recover magnetic substances such as iron, nickel and cobalt, etc. The Chinese patent application CN101220412A adopted pre-roasting and vacuum distillation to separate cadmium, after refining, the refined cadmium was produced, and the ferronickel was recovered in the form of alloy. However, pyrometallurgy has problems such as high energy consumption, high investment cost, and low value of nickel-containing recovery products, etc.

The product recovered by the hydrometallurgy has high purity and good separation effect. The target metal in the waste Nickel-Cadmium battery is often leached by acid leaching, and then the corresponding metal is recovered by extraction or electrodeposition. For example, the Chinese patent application CN10141246B used electrolytic deposition to recover metal nickel and cadmium in Nickel-Cadmium battery leachate. The Chinese patent application CN100389520C used additives containing rare earth elements to precipitate and remove sodium ions from nickel sulfate solution. The Chinese patent application CN10131816A adopted pyrometallurgy-hydrometallurgy combination process, the metal cadmium in the waste Nickel-Cadmium battery was recovered by high-temperature distillation, and then used the P507 extractant to extract, separated and recovered cobalt and nickel. At the same time, new waste residues and waste salts were generated in the recovery process of the above-mentioned hydrometallurgy, and some of the metal elements were not recovered, resulting in secondary pollution.

Chinese patent CN1752232C extracted and separated nickel, magnesium and cobalt from the positive electrode waste leachate of impurity-removed waste Nickel-Cadmium battery. The method comprised the following steps: adjusting the pH value of the sulfuric acid leaching solution of the impurity-removed nickel-metal hydride and/or Nickel-Cadmium battery positive electrode waste to 4.5-5.0, carrying out fractional extraction on the leachate to transfer magnesium and cobalt into the organic phase and retain nickel in the aqueous phase, respectively washing nickel and magnesium, leading the washing liquid of magnesium out of the independent outlet to reach the separation of nickel, magnesium, cobalt, the organic phase consisted of mono(2-ethylhexyl) bis-(2-ethylhexyl)phosphonate as extractant and kerosene as diluent. However, this technology was only used for treating the cadmium-free waste Nickel-Cadmium battery positive electrode materials, the extractant was saponified with the sodium hydroxide, and then converted into nickel soap for use. The technical problems that the concentration of the sodium sulfate was gradually increased along with the extraction reaction process, the high-concentration sodium sulfate crystals plugged the pipe in the solution, and consequently extraction could not be carried out smoothly was not solved, and in the conversion process of the nickel soap and the sodium soap, a large amount of nickel-containing and salt-containing wastewater was generated.

SUMMARY

Aiming at the defects of the existing hydrometallurgy, the invention provides a method for regenerating raw materials of waste Nickel-Cadmium batteries based on solvent extraction. According to the method, low-cost and efficient recovery of valuable metal iron, cadmium, cobalt and nickel in the waste Nickel-Cadmium battery is realized by using solvent extraction technology which is easy to perform continuous operation, and meanwhile, the sodium introduced by the process is recycled. According to the invention, the flow of pretreatment+sulfuric acid leaching+P204 and DZ272 extraction separation+nitric acid stripping is adopted, the problem of crystallization plugging pipes generated by sodium saponification is effectively solved through accurate controlling parameters, cadmium nitrate, cobalt nitrate and nickel nitrate products conforming to the quality standard of raw materials for fully sintered Nickel-Cadmium battery are directly prepared, the main impurities iron and sodium elements are synchronously recovered in the form of the high-purity ferric oxalate and industrial-grade sodium sulfate as by-products, and waste residues and waste salt are not generated in the whole process.

In order to achieve the above object, the present invention adopts the following technical paths.

(1) Pretreatment: After the industrial waste Nickel-Cadmium battery is disassembled, clean water is used to rinse and disassemble the obtained waste polar plates, and then the waste polar plates are shredded.

(2) Leaching: The shredded waste electrode material is leached with sulfuric acid solution, and oxidizing agent is added during the leaching process to help dissolve.

(3) Extraction of iron: Taking the leaching solution obtained in step (2), adjusting the pH to 0.8-1.8, then adding the first extractant formed by mixing the P204 and the solvent oil, after extraction, the first raffinate and the organic phase(the first organic phase) loaded with iron and a small amount of cadmium are obtained. Washing the organic phase loaded with iron and a small amount of cadmium by using dilute sulfuric acid, and then strip with oxalic acid solution to obtain iron oxalate solution.

(4) Extracting cadmium: Taking the first raffinate, adjusting the pH to 2.0-3.0, adding the first extractant, and obtain the second raffinate and the organic phase (the second organic phase) loaded with cadmium and a small amount of cobalt and nickel by extracting; Washing the second organic phase loaded with cadmium and a small amount of cobalt and nickel by using cadmium sulfate solution, and then stripping with dilute nitric acid to obtain cadmium nitrate solution.

(5) Extracting cobalt: Taking the second raffinate, adjusting the pH to 4.5-5.5, adding the second extractant formed by mixing DZ272 and solvent oil, and obtain the third raffinate and the organic phase (the third organic phase) loaded with cobalt and a small amount of nickel by extraction; Washing the third organic phase loaded with cobalt and a small amount of nickel by using cobalt sulfate solution, and then stripping with the dilute nitric acid to obtain cobalt nitrate solution.

(6) Extracting nickel: Taking the third raffinate, adjusting the pH to 5.0-6.0, adding the first extractant, and obtain the fourth raffinate, namely sodium sulfate solution, and the organic phase (the fourth organic phase) loaded with nickel and a small amount of sodium by extraction; washing the fourth organic phase loaded with nickel and a small amount of sodium by using nickel sulfate solution, and then stripping with the dilute nitric acid to obtain nickel nitrate solution.

The application scope of the present invention includes, but is not limited to, cadmium-containing, nickel-containing waste, and cutting leftover materials generated in the production process of Nickel-Cadmium batteries. The waste materials and residues containing cadmium and nickel which is similar to columnar Nickel-Cadmium batteries, can also be treated by the method proposed in the present invention after conventional decontamination procedures.

In step (1), the dismantled industrial waste Nickel-Cadmium battery plates are rinsed with clean water to remove impurities such as KOH and LiOH adhering to the surface of the polar plates, thereby reducing the processing burden of subsequent steps. Then, the cleaned waste plate is shredded to reduce the particle size of the material, and the subsequent acid leaching effect is ensured.

Preferably, in step (1), the cleaning method of the polar plate is 3 to 5 stages of counter-current rinsing with clean water.

Preferably, in step (1), the cleaned waste polar plate is shredded by two stages of a double-shaft wet shredder.

Further preferably, in step (1), the particle size of the polar plate after the shredding treatment should be −10×100 mm.

In step (2), the pretreated industrial waste Nickel-Cadmium battery electrode plate material is added to the sulfuric acid solution for leaching to obtain the sulfuric acid leaching solution containing elements such as Fe, Cd, Ni, Co, and Na etc. No Li ions are detected in the sulfuric acid leaching solution.

Preferably, in step (2), the solid-to-liquid ratio of the solid material to the sulfuric acid solution after crushing of the waste electrode is 1:5-12 (kg/L), the concentration of the sulfuric acid solution is 1.5-3 mol/L, and the temperature of the acid leaching process system is 343~368K, the acid leaching time is 6~24 h, the addition amount of 30% hydrogen peroxide is 6~12% of the volume of the mixed solution, and the stirring speed of the acid leaching is 150~300 rpm.

In step (3), the oxidant is added to convert $Fe2+$ in the leaching solution into $Fe3+$, and the pH is adjusted to 0.80-1.80. After the first extractant is used to extract iron from the sulfuric acid leaching solution of industrial waste Nickel-Cadmium batteries, most of $Fe3+$ and a small amount of $Cd2+$ enter the organic phase (first organic phase), and a large amount of $Cd2+$ remains in the first raffinate. The first raffinate contains elements such as cadmium, cobalt, nickel, and sodium. The first organic phase is washed with the dilute sulfuric acid, the co-extracted cadmium and entrained water can be removed, and the purity of the ferric in the organic phase is ensured. Then, the organic phase is stripped by oxalic acid to obtain the ferric oxalate solution.

Preferably, in step (3), the concentration of the P204 in the first extractant is 0.5-1.2 mol/L; the volume ratio of the first extractant (organic phase) to the sulfuric acid leaching solution (aqueous phase) is 1-2.5:1.

Preferably, in step (3), the amount of the oxidant added is 1.5-2 times the theoretical requirement of ferrous ions in the leaching solution.

Further preferably, in step (3), the oxidant is hydrogen peroxide.

Preferably, in step (3), the extraction and washing process is carried out at 288-298K, and the stripping operation is carried out at 308-323K.

Preferably, in step (3), the extraction stages are 3-7 stages. The washing stages are 1-3. The number of stripping stages is 3-7.

Preferably, in step (3), the concentration of the dilute sulfuric acid used in washing is 0.2-1.0 mol/L. The amount of oxalic acid in the oxalic acid solution used in stripping is 1.5-2.0 times the molar amount of $Fe3+$ in the organic phase.

Preferably, in step (3), the ratio (O/A) of the washing control is 3-5:1. The ratio (O/A) of the stripping control is 3-5:1.

Preferably, in step (3), the iron oxalate solution obtained by stripping can be evaporated and concentrated to prepare iron oxalate crystals; the organic phase generated by the stripping is the first extractant, which can be returned to the corresponding extraction section for recycling after saponification.

In step (4), after the cadmium in the first raffinate is extracted with the first extractant, most of the $Cd2+$ and a small amount of $Co2+$ and $Ni2+$ enter the organic phase (the second organic phase), and a large amount of Co2+ and Ni2+ remains in the second raffinate liquid. The second raffinate contains cobalt, nickel, sodium and other elements. Washing the second organic phase with the cadmium sulfate solution to remove co-extracted cobalt, nickel and entrained water, and ensure the purity of cadmium in the organic phase. Then, stripping the organic phase with the dilute nitric acid to obtain the cadmium nitrate solution.

Preferably, in step (4), the concentration of P204 in the first extractant is 0.5-1.2 mol/L; the volume ratio of the first extractant (organic phase) and the first raffinate (aqueous phase) is 1-1.5:1.

Preferably, in step (4), the initial pH of the first raffinate is adjusted to 2.0-3.0 by using sodium hydroxide solution.

Preferably, in step (4), the extraction, washing and stripping processes are carried out at the temperature of 288-298K.

Preferably, in step (4), the extraction stages are 3-7 stages. The washing stages are 3-5. The number of stripping stages is 3-5.

Preferably, in step (4), the concentration of cadmium in the cadmium sulfate solution used for washing is 1.5-2 g/L, and the pH of the cadmium sulfate solution is adjusted to 1.5-2.2 with the sulfuric acid. The amount of nitric acid in the dilute nitric acid solution used for stripping is 2-2.5 times the molar amount of Cd2+ in the organic phase.

Preferably, in step (4), the ratio (O/A) controlled in the washing process is controlled to be 3-5:1. The ratio (O/A) controlled in the stripping is controlled to be 3-5:1.

Preferably, in step (4), the cadmium nitrate solution obtained by the stripping can be evaporated and concentrated to obtain the cadmium nitrate solution or cadmium nitrate crystal that meets the quality standards of the raw material of the Nickel-Cadmium battery; the organic phase generated by the stripping is the first extractant, which can be returned to the corresponding extraction section for recycling after saponification.

In step (5), after the cobalt in the second raffinate is extracted with the second extractant, most of the Co2+ and a small amount of Ni2+ enter the organic phase (third organic phase), and a large amount of Ni2+ remains in the third raffinate. The third raffinate contains nickel and sodium elements. Washing the third organic phase with the cobalt sulfate solution to remove co-extracted Ni2+ and entrained water, and ensuring the purity of cobalt in the organic phase. Then, stripping the organic phase with the dilute nitric acid to obtain the cobalt nitrate solution.

Preferably, in step (5), the concentration of DZ272 in the second extractant is 0.05-0.15 mol/L; the volume ratio of the second extractant (organic phase) and the second raffinate (aqueous phase) is 1:3~5.

Preferably, in step (5), the initial pH of the second raffinate is adjusted to 4.5-5.5 by using the sodium hydroxide solution.

Preferably, in step (5), the extraction operation is performed at 308-323K. Washing and stripping operations are carried out at 288-298K.

Preferably, in step (5), the extraction stages are 3-7 stages. The washing stages are 2-6. The number of stripping stages is 2-6.

Preferably, in step (5), the concentration of cobalt in the cobalt sulfate solution used for washing is 0.3-0.5 g/L, and the pH of the cobalt sulfate solution is adjusted to 5.0-6.0 with the sulfuric acid. The amount of nitric acid in the dilute nitric acid solution used for stripping is 2-2.5 times the molar amount of Co2+ in the organic phase.

Preferably, in step (5), the ratio (O/A) in the washing process is controlled to be 3-5:1. The ratio (O/A) of the stripping is controlled to be 3-8:1.

Preferably, in step (5), the cobalt nitrate solution obtained by the stripping can be evaporated and concentrated to obtain the cobalt nitrate solution or cobalt nitrate crystals that meets the quality standards of the raw materials for Nickel-Cadmium batteries; the organic phase generated by the stripping is the second extractant. After saponification, it can be returned to the corresponding extraction section for recycling.

In step (6), after the nickel in the third raffinate is extracted with the first extractant, most of the Ni2+ and a small amount of Na+ enter the organic phase (the fourth organic phase), while a large amount of Na+ remains in the fourth raffinate. The fourth raffinate is the sodium sulfate solution. Washing the fourth organic phase with the nickel sulfate solution to remove co-extracted Na+ and entrained water, and ensure the purity of nickel in the organic phase. Then, stripping the organic phase with the dilute nitric acid to obtain the nickel nitrate solution.

Preferably, in step (6), the concentration of P204 in the first extractant is 0.5-1.2 mol/L; the volume ratio of the first extractant (organic phase) and the third raffinate (aqueous phase) is 2-3:1.

Preferably, in step (6), the initial pH of the third raffinate is adjusted to 5.0-6.0 by using the sodium hydroxide solution.

Preferably, in step (6), the extraction operation is performed at 308-323K. Washing and stripping operations are carried out at 288-298K.

Preferably, in step (6), the number of extraction stages is 6-10. The washing stages are 2-6. The number of stripping stages is 2 to 6.

Preferably, in step (6), the concentration of nickel in the nickel sulfate solution used for washing is 20-23 g/L, and the pH of the nickel sulfate solution is adjusted to 5.0-6.0 with the sulfuric acid. The amount of nitric acid in the dilute nitric acid solution used in the stripping is 2-2.5 times the molar amount of Ni2+ in the organic phase.

Preferably, in step (6), the ratio (O/A) in the washing process is controlled to be 3-5:1. The ratio (O/A) of the stripping is controlled to be 3-5:1.

Preferably, in step (6), the fourth raffinate obtained by the extraction is the sodium sulfate solution, the temperature of the sodium sulfate solution needs to be kept at 308-323K, and the industrial grade sodium sulfate can be obtained after evaporation and concentration.

Preferably, in step (6), the nickel nitrate solution obtained by the stripping can be evaporated and concentrated to obtain the nickel nitrate solution or nickel nitrate crystals that meets the quality standards of the raw materials for Nickel-Cadmium batteries; the organic phase generated by the stripping is the first extractant. After saponification, it can be returned to the corresponding extraction section for recycling.

Preferably, in the present invention, the washing liquid in each extraction process will all return to step (2) after the washing process is completed.

Preferably, in the present invention, the extraction device is a multi-stage Mixer-settler, and the contact mode of the organic phase and the water phase is multi-stage counter-current.

Preferably, in steps (3) (4) (5) (6), the first extraction agent and the second extraction agent are both saponified with the sodium hydroxide solution before extraction.

In the present invention, the first organic phase is loaded with iron and cadmium; the second organic phase is loaded with cadmium, cobalt and nickel; the third organic phase is loaded with cobalt and nickel; the fourth organic phase is loaded with nickel and sodium; and the sodium sulfate solution is the fourth raffinate.

Compared with the prior art, the present invention has the following advantages and technical effects:

(1) A manufacturing method for synchronously recovering metal nitrate products such as cadmium, cobalt, nickel from waste Nickel-Cadmium batteries is invented. Aiming at the sulfuric acid leaching system of waste Nickel-Cadmium batteries, based on the solvent extraction technology that can be produced on a large scale and continuously, nitric acid stripping is used for the first time to directly prepare cadmium nitrate, cobalt nitrate and nickel nitrate products that meet the quality standards of battery raw materials. A full-life cycle of cadmium, cobalt and nickel elements in the Nickel-Cadmium battery is achieved.

(2) In the conventional nickel extraction process, there is a technical problem that as the extraction reaction proceeds, the concentration of sodium sulfate in the aqueous solution gradually increases, and the sodium sulfate with the corresponding concentration will block the pipe after crystallization, resulting in the unsmooth extraction. Chinese patent CN1752232A avoids this problem by converting sodium soap to nickel soap, but there is a large amount of high-salt wastewater that needs to be treated in the process of converting sodium soap to nickel soap. Through the method of controlling and adjusting the temperature of the extraction system, the invention effectively solves the difficulty of directly using sodium soap to easily crystallize and block the pipe. All extraction processes directly use sodium soap, which simplifies the cumbersome process of converting sodium soap to nickel soap in the existing nickel extraction process, and greatly reduces production costs.

(3) The pretreatment process of removing impurities (mainly iron) of CN1752232A, and the currently common iron removing process in the art, can generate a large amount of iron waste residues. According to the invention, the iron extraction with P204 process is adopted, the problem that the ferric iron is difficult to be stripped is solved, and the iron is recovered in the form of the product of high-purity ferric oxalate. According to the method, iron waste residues which are difficult to treat in the traditional removal process are converted into high-added-value products (high-purity ferric oxalate), so that the resource utilization of the main impurity iron is realized.

(4) The sodium elements introduced in the process of the present invention can all be completely recovered in the form of industrial-grade sodium sulfate as by-products. The problem that a large amount of salt-containing waste water is generated from traditional metal extraction of sodium soap is solved, and the process cost is saved.

(5) The test results of the embodiments of the invention show that the method realizes the harmless and resourceful utilization of valuable metals in waste Nickel-Cadmium batteries. According to the method, more than 99% of the metal in the waste electrode plate can be recycled, wherein the recovery rate of cadmium element is 99.91%, and the purity of cadmium product is over 99.50%; the recovery rate of cobalt element is 98.22%, and the purity of cobalt product is 99.50% above; the recovery rate of nickel element is 99.5%, and the purity of nickel product is above 99.50%. Simultaneously, the impurity iron is prepared as a high value-added product—ferric oxalate, the iron element recovery rate reaches 96.83%, and the purity of iron product is more than 99.50%. Compared with the prior art, the effect is very remarkable.

(6) The target metal recovery products of the invention are all nitrates. The purity of the recovered product is high, and the quality of the product meets the quality standard of the raw materials for the production of new batteries. Recycled products can be directly used in the production of new fully sintered Nickel-Cadmium batteries. The method provides a new source of raw materials (nickel nitrate, cadmium nitrate, cobalt nitrate etc.) for the manufacturing process of fully sintered Nickel-Cadmium batteries.

BRIEF DESCRIPTION OF DRAWING

The FIGURE is a process flow diagram of the invention

DETAILED DESCRIPTION OF THE EMBODIMENTS

The present disclosure will be further described below with reference to specific embodiments, but the claimed protection scope of the present disclosure is not limited to the scope described in the embodiments.

Embodiment 1

Referring to the process flow diagram in the FIGURE, a method for regenerating raw materials from waste Nickel-Cadmium batteries based on solvent extraction includes the following steps.

(1) Pretreatment: After the industrial waste Nickel-Cadmium battery was disassembled, the positive and negative plates of the waste Nickel-Cadmium battery were obtained. The waste electrode plate was rinsed and cleaned with 4-stage countercurrent water to remove impurities such as KOH and LiOH adhering to the surface of the electrode plate. Then, the cleaned waste plates were shredded with a double-shaft shredder. The maximum particle size of the plate after shredding was −10×100 mm.

(2) Leaching: After the waste electrode was crushed, the material was leached with sulfuric acid, and hydrogen peroxide was added to assist in the leaching process. The concentration of the sulfuric acid was 2 mol/L, and the solid-liquid ratio of the solid material mixed with the sulfuric acid solution was 1:10 (unit: kg/L). In the acid leaching process, the system temperature was 358K, the acid leaching time was 8 h, the addition amount of hydrogen peroxide (30% by volume) was 10% of the total volume, and the stirring speed in the acid leaching process was 300 rpm. After the acid leaching was completed, the insoluble residue was filtered first, and then the leachate was collected. The total volume mentioned above was the sum of the volumes of all liquids.

The main concentrations in the sulfuric acid leaching solution of square waste Nickel-Cadmium batteries are shown in Table 1.

TABLE 1

| Concentration of each metal element in sulfuric acid leaching solution | | | |
| --- | --- | --- | --- |
| Metal Element | Concentration (g/L) | Metal Element | Concentration (g/L) |
| Fe | 12.250 | K | 0.060 |
| Co | 0.520 | Li | Not detected |
| Ni | 56.295 | Zn | 0.016 |
| Cd | 23.275 | Cu | 0.015 |
| Na | not detected | Mn | 0.040 |
| Mg | 0.390 | Al | 0.050 |
| Ca | 0.305 | Pb | 0.010 |

(3) Extraction of iron: P204 was used as the extractant for iron removal, it was diluted with 260 #solvent oil (sulfonated kerosene) to a concentration of 0.9 mol/L, that was, the first extractant, and NaOH solution (mass fraction 30%) was used at a saponification rate of 50%, homogeneous saponification was carried out to obtain the saponified first extractant. Oxidant hydrogen peroxide was added to the leaching solution obtained in step (2) to oxidize $Fe2+$ to $Fe3+$, and the amount of oxidant added was double of the theoretical requirement of ferrous ions in the leaching solution. The pH of the leachate was adjusted to 1.0 with sodium hydroxide. The 6-stage countercurrent extraction was performed at the temperature of 298K, the O/A ratio was controlled to 1.88:1, and the two-phase contact time was 15 min. After the extraction operation was completed, the first organic phase (loaded with iron and a small amount of cadmium) and the first raffinate were obtained, and most of the cadmium, cobalt and nickel remained in the first raffinate.

The first organic phase was washed with a sulfuric acid solution with a concentration of 0.5 mol/L at 298K for 2-stages countercurrent washing to remove co-extracted cadmium and entrained water, and the O/A ratio was 3:1 during washing to obtain the iron-loaded organic phase.

The iron-loaded organic phase after washing was stripped by using 6-stage countercurrent stripping with oxalic acid solution with a concentration of 0.52 mol/L at the temperature of 313K. The phase-ratio (O/A) was 3:1 to obtain the ferric oxalate solution. The organic phase generated by the stripping was the first extractant, which could be returned to the corresponding extraction section for recycling after saponification. The ferric oxalate solution obtained by the stripping could be evaporated and concentrated to prepare iron oxalate crystals. The recovery rate of iron element was 96.83%.

The concentration of each metal element in the ferric oxalate solution obtained by the stripping is shown in Table 2.

TABLE 2

| The Concentration of Each Metal Element in Ferric Oxalate Solution | | | |
| --- | --- | --- | --- |
| metal element | concentration (g/L) | metal element | concentration (g/L) |
| Fe | 19.004 | K | 0.002 |
| Co | not detected | Li | not detected |
| Ni | 0.009 | Zn | not detected |
| Cd | not detected | Cu | not detected |
| Na | 0.012 | Mn | not detected |

TABLE 2-continued

| The Concentration of Each Metal Element in Ferric Oxalate Solution | | | |
| --- | --- | --- | --- |
| metal element | concentration (g/L) | metal element | concentration (g/L) |
| Mg | not detected | Al | 0.002 |
| Ca | 0.001 | Pb | not detected |

(4) Extracting cadmium: The pH of the first raffinate was adjusted to 2.5 with sodium hydroxide, and the first extraction agent P204 with concentration of 0.9 mol/L and saponification rate of 50% was used as the extraction agent for cadmium extraction. The 6-stage countercurrent extraction was carried out at the temperature of 298K. The phase-ratio (O/A) was 0.88:1, and the two-phase contact time was 7 min. After the extraction process was completed, the second organic phase and the second raffinate were obtained. Most of the cobalt and nickel remained in the second raffinate.

A cadmium sulfate solution with the cadmium ion concentration of 1.63 g/L was taken as washing solution whose pH was adjusted to 2.0 by using the sulfuric acid. The second organic phase was subjected to the 5-stage countercurrent extraction at 298K to remove co-extracted cobalt, nickel, and entrained water. The phase-ratio (O/A) was 4:1 during washing, and the two-phase contact time was 5 min. After the washing process was completed, the cadmium-loaded organic phase was obtained.

The cadmium-loaded organic phase after washing was subjected to 3-stage countercurrent stripping with the dilute nitric acid solution with a concentration of 1.84 mol/L at 298K. The phase-ratio (O/A) was 4:1, and the two-phase contact time was 5 min. After the stripping was completed, the cadmium nitrate solution and the first extractant were obtained. After the first extractant was saponified, it was returned to the corresponding extraction section for recycling. The cadmium nitrate solution obtained by stripping could be evaporated and concentrated to obtain the cadmium nitrate solution or the cadmium nitrate crystal that meets the quality standards of the raw material of the Nickel-Cadmium battery. The recovery rate of cadmium element was 99.91%.

The concentration of each metal element in the cadmium nitrate solution obtained by the stripping is shown in Table 3.

TABLE 3

| the Concentration of Each Metal Element in Cadmium Nitrate Solution | | | |
| --- | --- | --- | --- |
| metal element | concentration (g/L) | metal element | concentration (g/L) |
| Fe | 0.002 | K | 0.001 |
| Co | 0.010 | Li | not detected |
| Ni | 0.063 | Zn | 0.002 |
| Cd | 100.858 | Cu | not detected |
| Na | 0.035 | Mn | 0.067 |
| Mg | 0.015 | Al | not detected |
| Ca | 0.262 | Pb | not detected |

(5) Extracting cobalt: DZ272 was used as the cobalt extraction agent, and it was diluted with mineral spirits to the concentration of 0.11 mol/l, that was the second extraction agent. The second extractant was homogeneously saponified with NaOH (mass fraction 30%) at a saponification rate of 8% to obtain saponified second extractant. The pH of the second raffinate was adjusted to 5.25 with the sodium hydroxide, and then it was extracted by performing the 6-stages countercurrent extraction at the temperature of 313K. The phase-ratio (O/A) was 1:4, and the two-phase contact time was 7 min. After the extraction process was completed, the third organic phase and the third raffinate were obtained. Most of the nickel remained in the third raffinate.

A cobalt sulfate solution with the cobalt ion concentration of 0.45 g/L was taken as washing solution whose pH was adjusted to 5.5 by using the sulfuric acid. The third organic phase was subjected to the 3-stage countercurrent extraction at 298K to remove co-extracted nickel and entrained water. The phase-ratio (O/A) was 4:1 during washing. After the washing process was completed, the cobalt-loaded organic phase was obtained.

The cobalt-loaded organic phase after washing was subjected to 3-stage countercurrent stripping with dilute nitric acid solution with a concentration of 0.33 mol/l at 298K. The phase-ratio (O/A) was 7:1, and the two-phase contact time was 5 min. After the stripping was completed, cobalt nitrate solution and the second extractant were obtained. After the second extractant was saponified, it was returned to the corresponding extraction section for recycling. The cobalt nitrate solution obtained by stripping could be evaporated and concentrated to obtain the cobalt nitrate solution or the cobalt nitrate crystal that meets the quality standards of the raw material of the Nickel-Cadmium battery. The recovery rate of cobalt element was 98.22%.

The concentration of each metal element in the cobalt nitrate solution obtained by the stripping is shown in Table 4.

TABLE 4 the Concentration of Each Metal Element in Cobalt Nitrate Solution

| metal element | concentration (g/L) | metal element | concentration (g/L) |
|---|---|---|---|
| Fe | 0.001 | K | not detected |
| Co | 9.399 | Li | not detected |
| Ni | 0.026 | Zn | not detected |
| Cd | 0.032 | Cu | not detected |
| Na | 0.002 | Mn | not detected |
| Mg | 0.004 | Al | not detected |
| Ca | 0.002 | Pb | not detected |

(6) Extracting nickel: The pH of the third raffinate was adjusted to 5.25 with sodium hydroxide, and the first extraction agent P204 with concentration of 0.9 mol/L and saponification rate of 50% was used as the nickel extraction agent. The 8-stage countercurrent extraction was carried out at the temperature of 313K. The phase-ratio (O/A) was 2.24:1, the two-phase contact time was 7 min. After the extraction process was completed, the fourth organic phase and the fourth raffinate were obtained. Sodium irons still remained in the fourth raffinate.

A nickel sulfate solution with the nickel ion concentration of 21.4 g/L was taken as washing solution whose pH was adjusted to 5.25 by using the sulfuric acid. The fourth organic phase was subjected to the 5-stage countercurrent extraction at 298K to remove co-extracted sodium and entrained water. The phase-ratio (O/A) was 4:1 during washing. After the washing process was completed, the nickel-loaded organic phase was obtained.

The nickel-loaded organic phase after washing was subjected to 5-stage countercurrent stripping with the dilute nitric acid solution with a concentration of 3.10 mol/L at 298K. The phase-ratio (O/A) was 4:1. After the stripping was completed, nickel nitrate solution and the first extractant were obtained. After the first extractant was saponified, it was returned to the corresponding extraction section for recycling. The nickel nitrate solution obtained by stripping could be evaporated and concentrated to obtain the nickel nitrate solution or the nickel nitrate crystal that meets the quality standards of the raw material of the Nickel-Cadmium battery. The fourth raffinate could be evaporated and concentrated to obtain industrial grade sodium sulfate (GB/T6009-2014 industrial anhydrous sodium sulfate class III first-grade product). The recovery rate of nickel element was 99.58%.

The concentration of each metal element in the nickel nitrate solution and the sodium sulfate obtained by the stripping is shown in table 5 and 6.

TABLE 5 the Concentration of Each Metal Element in Nickel Nitrate Solution

| metal element | concentration (g/L) | metal element | concentration (g/L) |
|---|---|---|---|
| Fe | not detected | K | 0.003 |
| Co | 0.018 | Li | not detected |
| Ni | 88.250 | Zn | 0.005 |
| Cd | 0.004 | Cu | not detected |
| Na | 0.185 | Mn | not detected |
| Mg | 0.159 | Al | not detected |
| Ca | 0.018 | Pb | 0.014 |

TABLE 6 the Concentration of Each Metal Element in Sodium Sulfate Solution

| metal element | concentration (g/L) | metal element | concentration (g/L) |
|---|---|---|---|
| Fe | 0.090 | K | 0.045 |
| Co | 0.032 | Li | not detected |
| Ni | 0.755 | Zn | 0.006 |
| Cd | 0.172 | Cu | not detected |
| Na | 70.285 | Mn | not detected |
| Mg | 0.005 | Al | not detected |
| Ca | 0.011 | Pb | 0.002 |

Embodiment 2

(1) Pretreatment: After the industrial waste Nickel-Cadmium battery was disassembled, the positive and negative plates of the waste-Nickel-Cadmium battery were obtained. The waste electrode plate was rinsed and cleaned with 5-stage countercurrent water to remove impurities such as KOH and LiOH adhering to the surface of the electrode plate. Then, the cleaned waste plates were shredded with a double-shaft shredder. The maximum particle size of the plates after shredding was −10×100 mm.

(2) Leaching: After the waste electrode was crushed, the material was leached with sulfuric acid, and hydrogen peroxide was added to assist in the leaching process. The sulfuric acid concentration of the leachate was 1.80 mol/l, and the solid-liquid ratio of the solid material mixed with the sulfuric acid solution was 1:8 (unit: kg/L). During the acid leaching process, the system temperature was 343K, the acid leaching time was 12 h, the addition amount of hydrogen peroxide (30% by volume) was 8% of the total volume, and the stirring speed during the acid leaching process was 250 rpm. After the acid leaching was completed, the insoluble residue was filtered first, and then the leachate was collected. The total volume mentioned above was the sum of the volumes of all liquids.

The main concentrations in the sulfuric acid leaching solution of square waste Nickel-Cadmium batteries are shown in Table 7.

TABLE 7 the Concentration of Each Metal Element
in Sulfuric Acid Leaching Solution

| metal element | concentration (g/L) | metal element | concentration (g/L) |
| --- | --- | --- | --- |
| Fe | 15.030 | K | 0.045 |
| Co | 0.315 | Li | not detected |
| Ni | 31.030 | Zn | 0.237 |
| Cd | 52.640 | Cu | 0.002 |
| Na | not detected | Mn | 0.034 |
| Mg | 0.009 | Al | 0.007 |
| Ca | 0.017 | Pb | 0.017 |

(3) Extraction of iron: P204 was used as the extractant for iron removal, it was diluted with the solvent oil to a concentration of 1.0 mol/L, that was, the first extractant, and NaOH solution (mass fraction 30%) was used at saponification rate of 60%, homogeneous saponification was carried out to obtain the saponified first extractant. Oxidant hydrogen peroxide was added to the leaching solution obtained in step (2) to oxidize $Fe^{2+}$ to $Fe^{3+}$, and the amount of the oxidant added was 1.5 times the theoretical requirement of $Fe^{2+}$ in the leaching solution. The pH of the leachate was adjusted to 1.1 with the sodium hydroxide. The 6-stage countercurrent extraction was performed at the temperature of 293K, and the O/A ratio was controlled to 1.65:1, and the two-phase contact time was 15 min. After the extraction operation was completed, the first organic phase (loaded with iron and a small amount of cadmium) and the first raffinate were obtained, and most of the cadmium, cobalt and nickel remained in the first raffinate.

The first organic phase was washed with a sulfuric acid solution with concentration of 0.7 mol/l at 293K for 3-stage countercurrent washing to remove co-extracted cadmium and entrained water. The phase-ratio (O/A) was 4:1 during washing to obtain the ferric-loaded organic phase.

The iron-loaded organic phase after washing was stripped by using 5-stage countercurrent stripping with oxalic acid solution with a concentration of 1.0 mol/l at the temperature of 323K. The phase-ratio (O/A) was 4:1 to obtain ferric oxalate solution. The organic phase generated by the stripping was the first extractant, which could be returned to the corresponding extraction section for recycling after saponification. The ferric oxalate solution obtained by the stripping could be evaporated and concentrated to prepare iron oxalate crystals. The recovery rate of iron element was 97.48%.

The concentration of each metal element in the ferric oxalate solution obtained by the back extraction is shown in Table 8.

TABLE 8 the Concentration of Each Metal Element
in Ferric Oxalate Solution

| metal element | concentration (g/L) | metal element | concentration (g/L) |
| --- | --- | --- | --- |
| Fe | 35.769 | K | 0.003 |
| Co | not detected | Li | not detected |
| Ni | 0.006 | Zn | not detected |
| Cd | not detected | Cu | not detected |
| Na | 0.009 | Mn | not detected |
| Mg | not detected | Al | 0.001 |
| Ca | 0.004 | Pb | not detected |

(4) Extracting cadmium: The pH of the first raffinate was adjusted to 2.2 with the sodium hydroxide, and the first extraction agent P204 with concentration of 1.0 mol/L and saponification rate of 60% was used as the extraction agent for cadmium extraction. The 6-stage countercurrent extraction was carried out at the temperature of 293K. The phase-ratio (O/A) was 1.9:1, and the two-phase contact time was 7 min. After the extraction process was completed, the second organic phase and the second raffinate were obtained. Most of the cobalt and nickel remained in the second raffinate.

A cadmium sulfate solution with the cadmium ion concentration of 2.0 g/L was taken as washing solution whose pH was adjusted to 1.5 by using with the sulfuric acid. The second organic phase was subjected to the 4-stage countercurrent extraction at 298K to remove co-extracted cobalt, nickel, and entrained water. The phase-ratio (O/A) was 4:1 during washing, and the two-phase contact time was 5 min. After the washing process was completed, the cadmium-loaded organic phase was obtained.

The cadmium-loaded organic phase after washing was subjected to 4-stage countercurrent stripping with the dilute nitric acid solution with concentration of 2.4 mol/L at 293K. The phase-ratio (O/A) was 5:1, and the two-phase contact time was 5 min. After the stripping was completed, the cadmium nitrate solution and the first extractant were obtained. After the first extractant was saponified, it was returned to the corresponding extraction section for recycling. The cadmium nitrate solution obtained by stripping could be evaporated and concentrated to obtain the cadmium nitrate solution or the cadmium nitrate crystal that meets the quality standards of the raw material of the Nickel-Cadmium battery. The recovery rate of cadmium element was 99.45%.

The concentration of each metal element in the cadmium nitrate solution obtained by the stripping is shown in table 9.

TABLE 9 the Concentration of Each Metal Element
in Cadmium Nitrate Solution

| metal element | concentration (g/L) | metal element | concentration (g/L) |
| --- | --- | --- | --- |
| Fe | 0.002 | K | 0.003 |
| Co | 0.016 | Li | not detected |
| Ni | 0.049 | Zn | 0.006 |
| Cd | 130.869 | Cu | not detected |
| Na | 0.027 | Mn | 0.025 |
| Mg | 0.014 | Al | not detected |
| Ca | 0.152 | Pb | not detected |

(5) Extracting cobalt: DZ272 was used as the cobalt extraction agent, and it was diluted with mineral spirits to the concentration of 0.11 mol/l, that was the second extraction agent. The second extractant was homogeneously saponified with NaOH (mass fraction 30%) at a saponification rate of 5% to obtain saponified second extractant. The pH of the second raffinate was adjusted to 5.0 with the sodium hydroxide, and then it was extracting by performing the 5-stage countercurrent extraction at the temperature of 323K. The phase-ratio (O/A) was 1:5, and the two-phase contact time was 7 min. After the extraction process was completed, the third organic phase and the third raffinate were obtained. Most of the nickel remained in the third raffinate.

A cobalt sulfate solution with the cobalt ion concentration of 0.50 g/L was taken as washing solution whose pH was adjusted to 5.7 by using the sulfuric acid. The third organic phase is subjected to the 4-stage countercurrent extraction at 298K to remove co-extracted nickel and entrained water. The phase-ratio (O/A) is 5:1 during washing. After the washing process was completed, the cobalt-loaded organic phase is obtained.

The cobalt-loaded organic phase after washing was subjected to 3-stage countercurrent stripping with the dilute nitric acid solution with a concentration of 0.21 mol/l at 298K. The phase-ratio (O/A) was 5:1, the two-phase contact time was 5 min. After the stripping was completed, cobalt nitrate solution and the second extractant were obtained. After the second extractant was saponified, it was returned to the corresponding extraction section for recycling. The cobalt nitrate solution obtained by stripping could be evaporated and concentrated to obtain the cobalt nitrate solution or the cobalt nitrate crystal that meets the quality standards of the raw material of the Nickel-Cadmium battery. The recovery rate of cobalt element was 98.54%.

The concentration of each metal element in the cobalt nitrate solution obtained by the stripping is shown in Table 10.

TABLE 10

| | the Concentration of Each Metal Element in Cobalt Nitrate Solution | | |
|---|---|---|---|
| metal element | concentration (g/L) | metal element | concentration (g/L) |
| Fe | 0.002 | K | not detected |
| Co | 5.834 | Li | not detected |
| Ni | 0.019 | Zn | not detected |
| Cd | 0.024 | Cu | not detected |
| Na | 0.001 | Mn | not detected |
| Mg | 0.006 | Al | not detected |
| Ca | 0.003 | Pb | not detected |

(6) Extracting nickel: The pH of the third raffinate was adjusted to 5.5 with sodium hydroxide, and the first extraction agent P204 with concentration of 1.0 mol/L and saponification rate of 60% was used as the nickel extraction agent. The 10-stage countercurrent extraction was carried out at the temperature of 323K. The phase-ratio (O/A) was 2.1:1, and the two-phase contact time was 7 min. After the extraction process was completed, the fourth organic phase and the fourth raffinate were obtained. Sodium irons still remained in the fourth raffinate.

A nickel sulfate solution with the nickel ion concentration of 23.0 g/L was taken as washing solution whose pH was adjusted to 5.5 by using the sulfuric acid. The fourth organic phase was subjected to the 5-stage countercurrent extraction at 293K to remove co-extracted sodium and entrained water.

The phase-ratio (O/A) was 5:1 during washing. After the washing process was completed, the nickel-loaded organic phase was obtained.

The nickel-loaded organic phase after washing was subjected to 5-stage countercurrent stripping with the dilute nitric acid solution with a concentration of 2.3 mol/L at 293K. The phase-ratio (O/A) was 5:1. After the stripping was completed, nickel nitrate solution and the first extractant were obtained. After the first extractant was saponified, it was returned to the corresponding extraction section for recycling. The nickel nitrate solution obtained by stripping could be evaporated and concentrated to obtain the nickel nitrate solution or the nickel nitrate crystal that meets the quality standards of the raw material of the Nickel-Cadmium battery. The fourth raffinate could be evaporated and concentrated to obtain industrial grade sodium sulfate (GB/T6009-2014 industrial anhydrous sodium sulfate class III first-grade product). The recovery rate of nickel element was 99.21%.

The concentration of each metal element in the nickel nitrate solution and the sodium sulfate obtained by the stripping is shown in table 11 and 12.

TABLE 11

| | the Concentration of Each Metal Element in Nickel Nitrate Solution | | |
|---|---|---|---|
| metal element | concentration (g/L) | metal element | concentration (g/L) |
| Fe | not detected | K | 0.001 |
| Co | 0.013 | Li | not detected |
| Ni | 64.130 | Zn | 0.002 |
| Cd | 0.005 | Cu | not detected |
| Na | 0.114 | Mn | not detected |
| Mg | 0.187 | Al | not detected |
| Ca | 0.012 | Pb | 0.014 |

TABLE 12

| | the Concentration of Each Metal Element in Sodium Sulfate Solution | | |
|---|---|---|---|
| metal element | concentration (g/L) | metal element | concentration (g/L) |
| Fe | 0.054 | K | 0.023 |
| Co | 0.016 | Li | not detected |
| Ni | 0.323 | Zn | 0.007 |
| Cd | 0.172 | Cu | not detected |
| Na | 65.514 | Mn | not detected |
| Mg | 0.010 | Al | not detected |
| Ca | 0.007 | Pb | 0.009 |

Embodiment 3

(1) Pretreatment: After the industrial waste Nickel-Cadmium battery was disassembled, the positive and negative plates of the waste-Nickel-Cadmium battery were obtained. The waste electrode plate was rinsed and cleaned with 4-stage countercurrent water to remove impurities such as KOH and LiOH adhering to the surface of the electrode plate. Then, the cleaned waste plates are shredded with a double-shaft shredder. The maximum particle size of the plates after shredding was −10×100 mm.

(2) Leaching: After the waste electrode was crushed, the material was leached with sulfuric acid, and hydrogen peroxide was added to assist in the leaching process. The sulfuric acid concentration of the leachate was 2.2 mol/l, and the solid-liquid ratio of the solid material mixed with sulfuric acid solution was 1:12 (unit: kg/L). During the acid leaching process, the system temperature was 368K, the acid leaching time was 24 h, the addition amount of hydrogen peroxide (30% by volume) was 12% of the total volume, and the stirring speed during the acid leaching process was 200 rpm. After the acid leaching was completed, the insoluble residue was filtered first, and then the leachate was collected. The total volume mentioned above was the sum of the volumes of all liquids.

The main concentrations in the sulfuric acid leaching solution of square waste Nickel-Cadmium batteries are shown in Table 13.

TABLE 13

|  | the Concentration of Each Metal Element in Sulfuric Acid Leaching Solution | | |
| --- | --- | --- | --- |
| metal element | concentration (g/L) | metal element | concentration (g/L) |
| Fe | 10.560 | K | 0.030 |
| Co | 0.252 | Li | not detected |
| Ni | 43.312 | Zn | 0.027 |
| Cd | 12.830 | Cu | 0.036 |
| Na | 0.001 | Mn | 0.029 |
| Mg | 0.215 | Al | 0.024 |
| Ca | 0.285 | Pb | 0.015 |

(3) Extraction of iron: P204 was used as the extractant for iron removal, it was diluted with the 260 #solvent oil to a concentration of 0.7 mol/L, that was the first extractant, and NaOH solution (quality score 30%) was used at a saponification rate of 50%, homogeneous saponification was carried out to obtain the saponified first extractant. Oxidant hydrogen peroxide was added to the leaching solution obtained in step (2) to oxidize $Fe^{2+}$ to $Fe^{3+}$, and the amount of the oxidant added was 1.8 times the theoretical requirement of $Fe^{2+}$ in the leaching solution. The pH of the leachate was adjusted to 1.1 with sodium hydroxide. The 4-stage countercurrent extraction was performed at the temperature of 298K, the O/A ratio was controlled to 1.6:1, and the two-phase contact time was 15 min. After the extraction operation was completed, the first organic phase (loaded with iron and a small amount of cadmium) and the first raffinate were obtained, and most of the cadmium, cobalt and nickel remained in the first raffinate.

The first organic phase was washed with the sulfuric acid solution with a concentration of 0.3 mol/l at 298K for single-stage countercurrent washing to remove co-extracted cadmium and entrained water. The phase-ratio (O/A) was 5:1 during washing to obtain the ferric-loaded organic phase.

The ferric-loaded organic phase after washing was stripped by using 4-stage countercurrent stripping with the oxalic acid solution with a concentration of 0.55 mol/l at the temperature of 313K. The phase-ratio (O/A) was 3:1 to obtain ferric oxalate solution. The organic phase generated by the stripping was the first extractant, which could be returned to the corresponding extraction section for recycling after saponification. The ferric oxalate solution obtained by the stripping could be evaporated and concentrated to prepare iron oxalate crystals. The recovery rate of iron element was 97.12%.

The concentration of each metal element in the ferric oxalate solution obtained by the back extraction is shown in Table 14.

TABLE 14

|  | the Concentration of Each Metal Element in Ferric Oxalate Solution | | |
| --- | --- | --- | --- |
| metal element | concentration (g/L) | metal element | concentration (g/L) |
| Fe | 19.326 | K | 0.004 |
| Co | not detected | Li | not detected |
| Ni | 0.008 | Zn | not detected |
| Cd | not detected | Cu | not detected |
| Na | 0.009 | Mn | not detected |
| Mg | not detected | Al | 0.001 |
| Ca | 0.002 | Pb | not detected |

(4) Extracting cadmium: The pH of the first raffinate was adjusted to 2.7 with the sodium hydroxide, and the first extraction agent P204 with concentration of 0.7 mol/L and saponification rate of 50% was used as the extraction agent for cadmium extraction. The 4-stage countercurrent extraction was carried out at the temperature of 298K. The phase-ratio (O/A) was 0.65:1, the two-phase contact time was 7 min. After the extraction process was completed, the second organic phase and the second raffinate were obtained. Most of the cobalt and nickel remained in the second raffinate.

A cadmium sulfate solution with the cadmium ion concentration of 1.5 g/L was taken as washing solution whose pH was adjusted to 2.2 by using sulfuric acid. The second organic phase was subjected to the 3-stage countercurrent extraction at 298K to remove co-extracted cobalt, nickel, and entrained water. The phase-ratio (O/A) was 3:1 during washing, and the two-phase contact time was 5 min. After the washing process was completed, the cadmium-loaded organic phase was obtained.

The cadmium-loaded organic phase after washing was subjected to 3-stage countercurrent stripping with dilute nitric acid solution with a concentration of 0.90 mol/L at 298K. The phase-ratio (O/A) was 3:1, and the two-phase contact time was 5 min. After the stripping was completed, cadmium nitrate solution and the first extractant were obtained. After the first extractant was saponified, it was returned to the corresponding extraction section for recycling. The cadmium nitrate solution obtained by stripping could be evaporated and concentrated to obtain the cadmium nitrate solution or the cadmium nitrate crystal that meets the quality standards of the raw material of the Nickel-Cadmium battery. The recovery rate of cadmium element was 99.35%.

The concentration of each metal element in the cadmium nitrate solution obtained by the stripping is shown in table 15.

TABLE 15

|  | the Concentration of Each Metal Element in Cadmium Nitrate Solution | | |
| --- | --- | --- | --- |
| metal element | concentration (g/L) | metal element | concentration (g/L) |
| Fe | 0.001 | K | 0.002 |
| Co | 0.008 | Li | not detected |
| Ni | 0.035 | Zn | 0.001 |
| Cd | 49.541 | Cu | not detected |
| Na | 0.028 | Mn | 0.033 |

TABLE 15-continued

| the Concentration of Each Metal Element in Cadmium Nitrate Solution | | | |
|---|---|---|---|
| metal element | concentration (g/L) | metal element | concentration (g/L) |
| Mg | 0.012 | Al | not detected |
| Ca | 0.181 | Pb | not detected |

(5) Extracting cobalt: DZ272 was used as the cobalt extraction agent, and it was diluted with mineral spirits to the concentration of 0.07 mol/l, that was the second extraction agent. The second extractant was homogeneously saponified with NaOH (quality fraction 30%) at a saponification rate of 9% to obtain a saponified second extractant. The pH of the second raffinate was adjusted to 4.75 with the sodium hydroxide, and then it was extracting by performing the 4-stage countercurrent extraction at the temperature of 318K. The phase-ratio (O/A) was 1:4, and the two-phase contact time was 7 min. After the extraction process was completed, the third organic phase and the third raffinate were obtained. Most of the nickel remained in the third raffinate.

A cobalt sulfate solution with the cobalt ion concentration of 0.45 g/L was taken as washing solution whose pH was adjusted to 5.2 by using sulfuric acid. The third organic phase was subjected to the 3-stage countercurrent extraction at 298K to remove co-extracted nickel and entrained water. The phase-ratio (O/A) was 4:1 during washing. After the washing process was completed, the cobalt-loaded organic phase was obtained.

The cobalt-loaded organic phase after washing was subjected to 4-stage countercurrent stripping with the dilute nitric acid solution with a concentration of 0.13 mol/l at 298K. The phase-ratio (O/A) was 6:1, and the two-phase contact time was 5 min. After the stripping was completed, cobalt nitrate solution and the second extractant were obtained. After the second extractant was saponified, it was returned to the corresponding extraction section for recycling. The cobalt nitrate solution obtained by stripping could be evaporated and concentrated to obtain the cobalt nitrate solution or the cobalt nitrate crystal that meets the quality standards of the raw material of the Nickel-Cadmium battery. The recovery rate of cobalt element was 98.65%.

The concentration of each metal element in the cobalt nitrate solution obtained by the stripping is shown in Table 16.

TABLE 16

| the Concentration of Each Metal Element in Cobalt Nitrate Solution | | | |
|---|---|---|---|
| metal element | concentration (g/L) | metal element | concentration (g/L) |
| Fe | not detected | K | not detected |
| Co | 3.786 | Li | not detected |
| Ni | 0.031 | Zn | not detected |
| Cd | 0.027 | Cu | not detected |
| Na | 0.005 | Mn | not detected |
| Mg | 0.003 | Al | not detected |
| Ca | 0.001 | Pb | not detected |

(6) Extracting nickel: The pH of the third raffinate was adjusted to 5.7 with sodium hydroxide, and the first extraction agent P204 with concentration of 0.9 mol/L and saponification rate of 50% was used as the nickel extraction agent. The 9-stage countercurrent extraction was carried out at the temperature of 318K. The phase-ratio (O/A) was 2.1:1, and the two-phase contact time was 7 min. After the extraction process was completed, the fourth organic phase and the fourth raffinate were obtained. Sodium irons still remained in the fourth raffinate.

A nickel sulfate solution with the nickel ion concentration of 20.5 g/L was taken as washing solution whose pH was adjusted to 5.25 by using the sulfuric acid. The fourth organic phase was subjected to the 5-stage countercurrent extraction at 298K to remove co-extracted sodium and entrained water. The phase-ratio (O/A) was 4:1 during washing. After the washing process was completed, the nickel-loaded organic phase was obtained.

The nickel-loaded organic phase after washing was subjected to 6-stage countercurrent stripping with dilute nitric acid solution with a concentration of 2.6 mol/L at 298K. The phase-ratio (O/A) was 4:1. After the stripping was completed, nickel nitrate solution and the first extractant were obtained. After the first extractant was saponified, it was returned to the corresponding extraction section for recycling. The nickel nitrate solution obtained by stripping could be evaporated and concentrated to obtain the nickel nitrate solution or the nickel nitrate crystal that meets the quality standards of the raw material of the Nickel-Cadmium battery. The fourth raffinate could be evaporated and concentrated to obtain industrial grade sodium sulfate (GB/T6009-2014 industrial anhydrous sodium sulfate class III first-grade product). The recovery rate of nickel element was 99.33%.

The concentration of each metal element in the nickel nitrate solution and the sodium sulfate obtained by the stripping is shown in table 17 and 18.

TABLE 17

| the Concentration of Each Metal Element in Nickel Nitrate Solution | | | |
|---|---|---|---|
| metal element | concentration (g/L) | metal element | concentration (g/L) |
| Fe | not detected | K | not detected |
| Co | 0.010 | Li | not detected |
| Ni | 74.934 | Zn | 0.002 |
| Cd | 0.002 | Cu | not detected |
| Na | 0.115 | Mn | not detected |
| Mg | 0.120 | Al | not detected |
| Ca | 0.013 | Pb | 0.005 |

TABLE 18

| the Concentration of Each Metal Element in Sodium Sulfate Solution | | | |
|---|---|---|---|
| metal element | concentration (g/L) | metal element | concentration (g/L) |
| Fe | not detected | K | 0.021 |
| Co | 0.012 | Li | not detected |
| Ni | 0.125 | Zn | 0.003 |
| Cd | 0.085 | Cu | not detected |
| Na | 55.586 | Mn | not detected |
| Mg | 0.003 | Al | not detected |
| Ca | 0.008 | Pb | not detected |

The present invention has been described in detail in the above embodiments, and it should not be understood that the scope of the subject matter of the present invention is only limited to the embodiments described above. Any implementation technology based on the above content shall fall within the scope of the present invention.

What is claimed is:

1. A method for regenerating raw materials of waste Nickel-Cadmium batteries based on a solvent extraction comprising the following steps:

1) disassembling, rinsing, and shredding an industrial waste cadmium-nickel battery to obtain a material;

2) leaching the material with a sulfuric acid solution to obtain a leachate;

3) taking the leachate obtained in step 2, adding a first oxidizing agent to the leachate to oxidize $Fe^{2+}$ in the leachate to $Fe^{3+}$, adjusting a pH to 0.8-1.8, adding a first extractant, and extracting to obtain a first raffinate and a first organic phase; washing the first organic phase with dilute sulfuric acid, and stripping with an oxalic acid solution to obtain an iron oxalate solution;

4) adjusting a pH of the first raffinate to 2.0-3.0, adding the first extractant to the first raffinate for a first extraction to obtain a second raffinate and a second organic phase; washing the second organic phase with a cadmium sulfate solution, and stripping with a dilute nitric acid solution to obtain a cadmium nitrate solution;

5) adjusting a pH of the second raffinate to 4.5-5.5, and adding a second extractant for a second extraction to obtain a third raffinate and a third organic phase; washing the third organic phase with a cobalt sulfate solution, and stripping with the dilute nitric acid solution to obtain a cobalt nitrate solution;

6) adjusting a pH of the third raffinate to 5.0-6.0, and adding the first extractant to the third raffinate for a third extraction to obtain a sodium sulfate solution and a fourth organic phase; washing the fourth organic phase with a nickel nitrate solution, and stripping with the dilute nitric acid solution to obtain a resulting nickel nitrate solution; wherein the first extractant is formed by mixing P204 and a solvent oil, and the second extractant is formed by mixing DZ272 and the solvent oil; and the first extractant and the second extractant are saponified when used.

2. The method according to claim 1, wherein in step 1, a content of K, Li and Ca elements in a waste electrode plate obtained from the step of disassembling, rinsing, and shredding the industrial waste cadmium-nickel battery is less than 0.01 wt %, wherein the waste electrode plate is treated with a two-stage wet shredding, a maximum particle size of a shredded industrial waste cadmium-nickel battery is 10×100 mm, and a moisture content of the shredded industrial waste cadmium-nickel battery is less than 10%.

3. The method according to claim 1, wherein in step 2, a mixing ratio of the material to the sulfuric acid solution is 1:5-1:12, a concentration of the sulfuric acid solution is 1.5-3.0 mol/l, a temperature of an acid leaching process is 343-368K, and an acid leaching time is 6-24 h, wherein leaching further comprises stirring during the leaching at a stirring speed of 150-300 rpm.

4. The method according to claim 1, wherein in step 2, the step of leaching the material further comprises adding a second oxidizing agent to facilitate a dissolution of the material, wherein the second oxidizing agent is a hydrogen peroxide solution, and a concentration of the hydrogen peroxide solution is 30-40%, and an addition amount of the hydrogen peroxide solution is 6-12% of a volume of the leachate in step 2.

5. The method according to claim 1, wherein in step 3, the first oxidizing agent is hydrogen peroxide, and an amount of the first oxidizing agent added is 1.2-2 times a molar amount of ferrous ions in a leaching solution; wherein extracting is performed 3-7 times, the washing is performed 1-3 times, and stripping is performed 3-7 times; and each stripping is performed at 308-323K; extracting and washing operations are performed at 288-298K; and an amount of oxalic acid in the oxalic acid solution is 1.5-2 times a molar amount of the $Fe^{3+}$ in the first organic phase.

6. The method according to claim 1, wherein in step 4, the first extraction is performed 3-7 times, the washing is performed 3-5 times, and the stripping is performed 3-5 times; wherein an amount of nitric acid in the dilute nitric acid solution is 2-2.5 times a molar amount of $Cd^{2+}$ in the second organic phase; and the cadmium nitrate solution obtained by stripping is evaporated and concentrated to obtain the cadmium nitrate solution or a cadmium nitric crystal.

7. The method according to claim 1, wherein in step 5), the second extraction is performed 3-7 times, the washing is performed 2-6 times, and the stripping is performed 2-6 times; wherein the second extraction is performed at 308-323K, and the stripping and the washing are performed at 288-298K; wherein an amount of nitric acid in the dilute nitric acid solution is 2-2.5 times a molar amount of $Co^{2+}$ in the third organic phase; and wherein the cobalt nitrate solution obtained by stripping is evaporated and concentrated to obtain the cobalt nitrate solution or a cobalt nitric crystal.

8. The method according to claim 1, wherein in step 6), the third extraction is performed 6-10 times; the washing is performed 2-6 times; and the stripping is performed 2-6 times; wherein the third extraction is performed at 308-323K, the stripping and the washing are performed at 288-298K; and wherein an amount of nitric acid in the dilute nitric acid solution is 2-2.5 times a molar amount of $Ni^{2+}$ in the fourth organic phase, and the resulting nickel nitrate solution obtained by stripping is evaporated and concentrated to obtain the resulting nickel nitrate solution or a nickel nitric crystal.

9. The method according to claim 1, wherein the first extractant or the second extractant is saponified with a sodium hydroxide solution having a mass fraction of 25-35%; a concentration of the P204 in the first extractant is 0.5-1.2 mol/L; and a concentration of the DZ272 in the second extractant is 0.05-0.15 mol/L.

10. The method according to claim 1, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

11. The method according to claim 2, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

12. The method according to claim 3, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

13. The method according to claim 4, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

14. The method according to claim 5, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

15. The method according to claim 6, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

16. The method according to claim 7, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

17. The method according to claim 8, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

18. The method according to claim 9, wherein the solvent oil is a 230 #solvent oil or a 260 #solvent oil (sulfonated kerosene); the sodium sulfate solution is kept at a temperature of 308-323K, and an industrial grade sodium sulfate is obtained after an evaporation and a concentration of the sodium sulfate solution.

\* \* \* \* \*